United States Patent
Ridden et al.

(10) Patent No.: US 11,185,511 B2
(45) Date of Patent: *Nov. 30, 2021

(54) ANTIFUNGAL TOPICAL COMPOSITION AND METHODS OF TREATMENT

(71) Applicant: BLUEBERRY THERAPEUTICS LIMITED, Macclesfield (GB)

(72) Inventors: John Ridden, Macclesfield (GB); Michael Davies, Macclesfield (GB); Liam Good, London (GB)

(73) Assignee: BLUEBERRY THERAPEUTICS LIMITED, Cheshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/023,602

(22) PCT Filed: Sep. 25, 2014

(86) PCT No.: PCT/GB2014/052911
§ 371 (c)(1),
(2) Date: Mar. 21, 2016

(87) PCT Pub. No.: WO2015/044669
PCT Pub. Date: Apr. 2, 2015

(65) Prior Publication Data
US 2016/0206567 A1   Jul. 21, 2016

(30) Foreign Application Priority Data

Sep. 25, 2013  (GB) .................................. 1317005
Nov. 25, 2013  (GB) .................................. 1320723

(51) Int. Cl.
*A61K 9/51*      (2006.01)
*A61K 31/137*    (2006.01)
(Continued)

(52) U.S. Cl.
CPC .......... *A61K 9/5146* (2013.01); *A61K 9/0014* (2013.01); *A61K 9/0021* (2013.01);
(Continued)

(58) Field of Classification Search
CPC ............... A61P 31/10; A61M 37/0015; A61M 2037/0023; A61K 9/5146; A61K 9/0014;
(Continued)

(56) References Cited

U.S. PATENT DOCUMENTS 6,500,446 B1 * 12/2002 Derrieu .................. A01N 25/10
424/401
7,462,362 B2 * 12/2008 Kepka ...................... A61K 8/41
424/401
(Continued)

FOREIGN PATENT DOCUMENTS

CN       101724284 A   *   6/2010
JP       2011-194189       10/2011
(Continued)

OTHER PUBLICATIONS

Tien et al. (abstract) Treatment of Acanthamoeba keratitis combined with fungal infection with polyhexamethylene biguanidine. The kaohsiung Journal of Medical Sciences, 15(11):665-673, Nov. 1, 1999.*

(Continued)

*Primary Examiner* — Lakshmi S Channavajjala
(74) *Attorney, Agent, or Firm* — Stephen J. Weyer, Esq.; Stites & Harbison, PLLC

(57) ABSTRACT

The present invention relates to a topical composition (and methods of producing the such compositions) for the treatment of a fungal infection comprising a polymer capable of forming nanoparticles and an antifungal agent. The invention also relates to novel uses of polyhexamethylene biguanide.

9 Claims, 10 Drawing Sheets

(51) Int. Cl.
| | |
|---|---|
| *A61K 9/00* | (2006.01) |
| *A61K 31/4745* | (2006.01) |
| *A61K 31/496* | (2006.01) |
| *A61K 31/7048* | (2006.01) |
| *A61M 37/00* | (2006.01) |

(52) U.S. Cl.
CPC .......... *A61K 9/5123* (2013.01); *A61K 31/137* (2013.01); *A61K 31/4745* (2013.01); *A61K 31/496* (2013.01); *A61K 31/7048* (2013.01); *A61M 37/0015* (2013.01); *A61M 2037/0023* (2013.01)

(58) Field of Classification Search
CPC .............. A61K 31/4745; A61K 31/496; A61K 31/7048; A61K 31/137
See application file for complete search history.

(56) References Cited

U.S. PATENT DOCUMENTS

| | | | |
|---|---|---|---|
| 7,871,649 B2* | 1/2011 | Modak | A01N 33/12 424/736 |
| 9,907,812 B2 | 3/2018 | Bapat et al. | |
| 10,238,683 B2 | 3/2019 | Good et al. | |
| 10,307,578 B2 | 6/2019 | Frederickson et al. | |
| 2002/0009491 A1 | 1/2002 | Rothbard et al. | |
| 2005/0249818 A1 | 11/2005 | Sawan et al. | |
| 2008/0312610 A1 | 12/2008 | Binks et al. | |
| 2010/0021530 A1* | 1/2010 | Weinfield | A61F 7/02 424/449 |
| 2010/0256568 A1 | 10/2010 | Frederickson et al. | |
| 2013/0115165 A1* | 5/2013 | Maitra | A61K 9/5138 424/1.37 |
| 2014/0242097 A1 | 8/2014 | Good et al. | |
| 2014/0364595 A1* | 12/2014 | Bapat | A61K 8/37 536/17.4 |
| 2015/0111971 A1* | 4/2015 | Evers | A61K 31/137 514/655 |
| 2017/0266428 A1 | 9/2017 | Frederickson et al. | |
| 2018/0214472 A1 | 8/2018 | Bapat et al. | |
| 2019/0142857 A1 | 5/2019 | Good et al. | |
| 2019/0240470 A1 | 8/2019 | Frederickson et al. | |

FOREIGN PATENT DOCUMENTS

| | | |
|---|---|---|
| JP | 2012-235899 | 12/2012 |
| WO | WO-2008062429 | 5/2008 |

OTHER PUBLICATIONS

Serrano et al. The use of natural antifungal compounds improves the beneficial effect of MAP in sweet cherry storage. Innovative Food Science and Emerging Technologies 6 (2005) 115-123.*
Walls et al., Successful use of locally applied polyhexamethylene biguanide as an adjunct to the treatment of fungal osteomyelitis, Can J Infect Dis Med Microbiol 2013;24(2):109-112. (Year: 2013).*
De Paula et al. Physical and chemcial characterization of poly(hexamethylene biguanidine) hydrochloride. Polymers 2011, 3, 928-941 (Year: 2011).*
International Search Report dated Dec. 10, 2014 in International Application No. PCT/GB2014/052911.
Gerit D Mulder, et al, "Polyhexamethylene Biguanide (PHMB): An Addendum to Current Topical Antimicrobials", Internet Citation, Jul. 1, 2007, pp. 1-11, XP002689622, ISSN: 1044-7946 Retrieved from the Internet: URL: http://www.woundsresearch.com/print/221 [retrieved on Dec. 18, 2012] p. 4, paragraph 2—p. 5, paragraph 2.
W. Behrens-Baumann, et al., "Keratitis", Ophthaimic Research, vol. 48, No. 4, Jan. 1, 2012 (Jan. 1, 2012), pp. 171-176, XP055157434, ISSN: 0030-3747, DOI: 10.1159/000337140 the whole document.
Hofmuller et al: Keratomycosis refractory to common therapy due to a Coelomycete not yet described treated successfully with PHMB in combination with systemic and local terbinafine. A case report. Mycoses, 2012, vol. 55, Supplement 4, p. 207. Abstract No. P361.
Markova T: Clinical inquiries. What is the most effective treatment for tinea pedis (athlete's foot)?. The Journal of Family Practice. Frontline Medical Communications 2002;51(1): 15-22.
Andrews et al: Common Tinea Infections in Children. Am Fam Physician 2008;77(10):1415-1420.
Newland & Abdel-Rahman: Update on terbinafine with a focus on dermatophytosis, Clinical, Cosmetic and Investigational Dermatology 2009:2 49-63.
Opponent Letter dated Jul. 23, 2021 in European Patent Application No. 14781264.8.

* cited by examiner

Particle size/relative intensity 3D plot

ANTIFUNGAL TOPICAL COMPOSITION AND METHODS OF TREATMENT

TECHNICAL FIELD OF THE INVENTION

The invention relates to a topical composition (and methods of producing such compositions) for the treatment of a fungal infection comprising a polymer capable of forming nanoparticles and an antifungal agent.

BACKGROUND TO THE INVENTION

Fungal infections are increasingly common in both human and animals, yet the treatment of such infections remains problematic due to toxicity of the antifungal compositions, poor solubility of such compositions and the remote location of some infections which can prove difficult to reach using traditional medicinal formulations.

A broad spectrum of antifungals such as amphotericin B, hamycin, filipin and nystatin were discovered in 1960s. But due to toxicity only hamycin and nystatin are used topically and amphotericin B systemically. A breakthrough in antifungal therapy was the introduction of azoles especially ketoconazole. The major classes of antifungals currently used are polyenes, azoles allyl amines, lipopeptides, and pyrimidines. However, polyenes are toxic to mammalian cells. Azoles are well tolerated topically but have side effects when given systemically and there have been several reports of resistance to azoles. Flucytosin is the most common pyrimidine used. Whilst it has excellent tissue penetration, resistance against flucytosine can develop rapidly and produce gastro intestinal side effects. Lipopetides display low toxicity and several trials are still on going to test efficacy.

The development of new antifungals is constrained because fungi are eukaryotic and cellular targets if disrupted can also damage host cells. The increase in fungal infections and increase in use of antifungals has resulted in emergence of resistance among fungi. Anti-fungal resistance has high clinical impact as fungal diseases are causing an increase in morbidity and mortality of immunocompromised patients.

It is estimated that around 40% of newly discovered drugs fail due to lack of proper delivery because of aqueous solubility problems. In the case of topical delivery of drugs, the barrier properties of skin often require permeation enhancers to achieve the required dose of drugs.

Onychomycosis (more commonly known as fungal nail infection) causes nails to thicken, discolor, disfigure, and split. Without treatment, the nails can become so thick that they press against the inside of the shoes, causing pressure, irritation, and pain. There are risks for further complications especially in patients with diabetes, those with peripheral vascular disease and the immunocompromised patient. Fungal nail infection may cause psychological and social problems. The incidence of fungal nail infection increases with age and has a prevalence of ~30% of the over 60 s with significant incidence in Europe with even higher levels in Asia. Fungal nail infection may affect one or more toenails and/or fingernails and can completely destroy the nail if left untreated.

The current treatment for fungal nail infection is as topical nail lacquer/paint (such as amorolfine) 1-2 times per week for 6-12 months and/or oral antifungals (such as terbinafine or itraconazole). Oral antifungals can have severe side effects such as gastro-intestinal upset and can even result in liver failure. Relapse is commonly reported in 25-50% of cases and many patients will not commit to the treatment course due to predicted side effects and length of treatment time and often only when disease becomes more aggressive will treatment begin. Current oral or topical treatments can take 6-12 months to work. Oral treatments have to saturate the systemic circulation to reach the toes and the increased doses increases the risk to the gastro-intestinal and liver complications. Topical treatments are ineffective at penetrating the thickened nail and again require high dosing.

Athlete's Foot (otherwise known as ringworm of the foot, Tinea pedis or moccasin foot) is a fungal infection of the skin generally caused by fungi in the genus *Trichophyton* (most commonly *T. rubrum* or *T. mentagrophytes*). The various parasitic fungi that cause athelete's foot also can cause other skin infection such as onychomycosis and Tinea cruris. Whilst distinct from fungal nail infection, athelete's foot also has issue with compliance and duration of treatment.

Aspergillosis is caused by an infection of the lungs caused by *Aspergillus* fungi. The infection is implicated in a number of conditions such as tuberculosis and chronic obstructive pulmonary disease. The infection can often be difficult to treat even when utilising a combination therapy approach. Increasingly, *Aspergillus* infections are resistant to triazoles.

Fungal keratitis is the inflammation of the cornea caused by a fungal infection. Natamycin ophthalmic suspension is often used for filamentous fungal infection, whereas Fluconazole ophthalmic solution is recommended for *Candida* infections. Amphotericin B eye drops are used for difficult to treat cases, however, these eye drops can be toxic in an individual.

Oral candidiasis is a fungal infection of the mucous membranes of the mouth by *Candida* species. It can be particularly problematic in immuno-deficient patients where it is often difficult to treat successfully.

An object of the present invention is to address one or more of the above problems associated with current antifungal treatments. It is also an object of the present invention to provide a topical anti-fungal treatment. It is additionally an object of the present invention to provide a treatment which allows for better penetration of the anti-fungal agent through a number of body tissues, such as the nail and/or dermis, mucosal membranes, and cornea and/or sclera.

SUMMARY OF THE INVENTION

In accordance with a first aspect of the present invention, there is provided a topical composition for the treatment of a fungal infection comprising a polymer capable of forming nanoparticles and an antifungal agent.

By forming nanoparticles from polymers and antifungal agents, the inventors have found advantageously that, the antifungal agents are taken up by the cells much more efficiently and thus can be formulated into a topical medicament having not only a slower release profile, but also a reduced therapeutic dose which can be delivered locally rather than systemically thus removing the danger of some orally administered antifungal agents. By combining a safe nanopolymer delivery system with a potent, antifungal agent, a topical treatment can be provided that can improve efficacy and potentially reduce current treatment timelines for infections from 6 months to 6 weeks.

The term "topical composition" is intended to mean a composition which is (or can be) applied to an exterior surface of the body surface, such as skin, nails, eyes, bronchioles, mucosal membranes, mouth and gastrointestinal tract.

The term "nanoparticle" is intended to mean a structure having an average diameter in the approximate range of 0.5-200 nm. Preferably, the nanoparticles will be in the range of 1 to 150 nm, more preferably in the range of 2 to 120 nm and most preferably 5 to 120 nm. In some instances, it is preferred that the nanoparticles are in an upper range of around 100 to 120 nm, more preferred in the range of 50 to 175 nm, even more preferred in the range of 75 to 150 nm and most preferred in the range of 110 to 140 nm. In other instances, it is preferred that the nanoparticles are in a lower range of 0.5 to 10 nm, more preferred in the range of 0.5 to 8 nm, even more preferred 1 to 7 nm and most preferred about 7 nm or lower. The term "antifungal agent" is intended to cover a range of compounds and molecules which are capable of inhibiting growth and/or survival of fungi causing a fungal infection.

It is preferred that the polymer comprises a linear and/or branched or cyclic polymonoguanide/polyguanidine, polybiguanide, analogue or derivative thereof. The linear and/or branched or cyclic polymonoguanide/polyguanidine, polybiguanide, analogue or derivative thereof may be according to the following formula 1a or formula 1b, with examples provided in tables A and B below:

$$N\{L_1\text{---}G_1\text{---}L_2\text{---}G_2\}_n G_3 \quad \text{Formula 1a}$$

$$\begin{array}{c} \text{---}(L_3)_n\text{---}(L_4)_n\text{---} \\ | \quad\quad | \\ (X) \quad\quad (X) \\ | \quad\quad | \\ (G_4) \quad\quad (G_5) \end{array} \quad \text{Formula 1b}$$

wherein:

"n", refers to number of repeating units in the polymer, and n can vary from 2 to 1000, for example from 2 or 5 to 10, 20, 30, 40, 50, 60, 70, 80, 90, 100, 150, 200, 250, 300, 350, 400, 450, 500, 600, 700, 800 or 900;

$G_1$ and $G_2$ independently represent a cationic group comprising biguanide or guanidine, wherein $L_1$ and $L_2$ are directly joined to a Nitrogen atom of the guanide. Thus, the biguanide or guanidine groups are integral to the polymer backbone. The biguanide or guanidine groups are not side chain moieties in formula 1a.

Example of Cationic Groups:

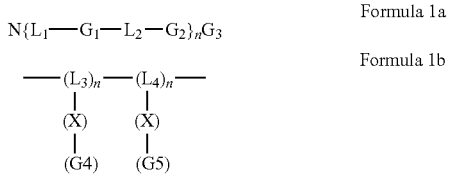

In the present invention, $L_1$ and $L_2$ are the linking groups between the $G_1$ and $G_2$ cationic groups in the polymer. $L_1$ and $L_2$ can independently represent an aliphatic group containing $C_1$-$C_{140}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$, -$C_{60}$, -$C_{70}$, -$C_{80}$, -$C_{90}$, -$C_{100}$, -$C_{110}$, -$C_{120}$, -$C_{130}$ or -$C_{140}$, alkyl; or $L_1$ and $L_2$ can (independently) be $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$, -$C_{60}$, -$C_{70}$, -$C_{80}$, -$C_{90}$, -$C_{100}$, -$C_{110}$, -$C_{120}$, -$C_{130}$ or -$C_{140}$), cycloaliphatic, heterocyclic, aromatic, aryl, alkylaryl, arylalkyl, oxyalkylene radicals, or $L_1$ and $L_2$ can (independently) be a polyalkylene radical optionally interrupted by one or more, preferably one, oxygen, nitrogen or sulphur atoms, functional groups as well as saturated or unsaturated cyclic moiety. Examples of suitable $L_1$ and $L_2$ are groups are listed in table A.

$L_1$, $L_2$, $G_1$ and $G_2$ may have been modified using aliphatic, cycloaliphatic, heterocyclic, aryl, alkaryl, and oxyalkylene radicals.

N and $G_3$ are preferably end groups. Typically the polymers of use in the invention have terminal amino (N) and cyanoguanidine ($G_3$) or guanidine ($G_3$) end groups. Such end groups may be modified (for example with 1,6-diaminohexane, 1,6 di(cyanoguanidino)hexane, 1,6-diguanidinohexane, 4-guanidinobutyric acid) by linkage to aliphatic, cycloaliphatic heterocyclic, heterocyclic, aryl, alkylaryl, arylalkyl, oxyalkylene radicals. In addition, end groups may be modified by linkage to receptor ligands, dextrans, cyclodextrins, fatty acids or fatty acid derivatives, cholesterol or cholesterol derivatives or polyethylene glycol (PEG). Optionally, the polymer can end with guanidine or biguanide or cyanoamine or amine or cyanoguanidine at N and $G_3$ positions or cyanoamine at N and cyanoguanidine at $G_3$ position or guanidine at N and Cyanoguanide at $G_3$ positions or L1 amine at G3 and cyanoguanidine at N. G3 can be $L_1$-amine, $L_2$-cyanoguanidine or $L_2$-guanidine. Depending on the number of polymerization (n) or polymer chain breakage and side reactions during synthesis, heterogeneous mixture of end groups can arise as described above as an example. Thus, the N and G3 groups can be interchanged/present as a heterogeneous mixture, as noted above. Alternatively N and $G_3$ may be absent and the polymer may be cyclic, in which case the respective terminal $L_1$ and $G_2$ groups are linked directly to one another.

In formula 1b, X can be either present or absent. $L_3$, $L_4$ and X are as noted above for "$L_1$ or $L_2$". In Thus, $L_3$ and $L_4$ and X are the linking groups between the $G_4$ and $G_5$ cationic groups in the polymer. $L_3$ and $L_4$ and X can independently represent an aliphatic group containing $C_1$-$C_{140}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$, -$C_{60}$, -$C_{70}$, -$C_{80}$, -$C_{90}$, -$C_{100}$, -$C_{110}$, -$C_{120}$, -$C_{130}$ or -$C_{140}$, alkyl; or $L_3$ and $L_4$ and X can independently be $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, -$C_{20}$, -$C_{30}$, -$C_{40}$, -$C_{50}$, -$C_{60}$, -$C_{70}$, -$C_{80}$, -$C_{90}$, -$C_{100}$, -$C_{110}$, -$C_{120}$, -$C_{130}$ or -$C_{140}$), cycloaliphatic, heterocyclic, aromatic, aryl, alkylaryl, arylalkyl, oxyalkylene radicals, or $L_3$ and $L_4$ and X can independently be a polyalkylene radical optionally interrupted by one or more, preferably one, oxygen, nitrogen or sulphur atoms, functional groups as well as saturated or unsaturated cyclic moiety. Examples of suitable $L_3$ and $L_4$ and X are groups are listed in table B.

"$G_4$" and "$G_5$" are cationic moieties and can be same or different. At least one of them is a biguanidine moiety or carbamoylguanidine, and the other moiety may be as above (biguanidine or carbamoylguanidine) or amine. For the avoidance of doubt, in formula 1b, cationic moiety $G_4$ and $G_5$ do not contain only single guanidine groups. For example, $G_4$ and $G_5$ typically do not contain single guanidine groups. Examples of such compounds are polyallylbiguanide, poly(allylbiguanidnio-co-allylamine), poly(allylcarbamoylguanidino-co-allylamine), polyvinylbiguanide, as listed in table B. Example of polyallylbiguanide is as shown below:

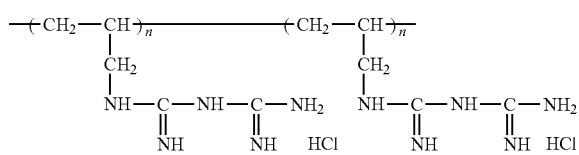

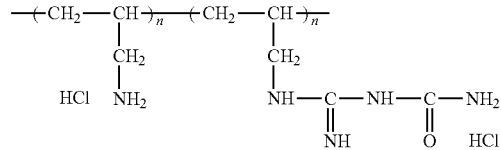

In case of polyallylbigunidine $L_3$ and $L_4$ are identical, $G_4$ and G5 are similar, thus polyallylbiguanide can be simplified as below.

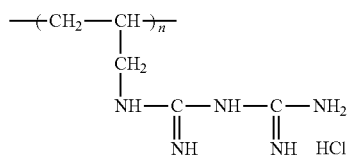

Example of poly(allylcarbamoylguanidnio-co-allylamine) is as shown below

The polymers for use in the invention will generally have counter ions associated with them. Suitable counter ions include but are not limited to the following: halide (for example chloride), phosphate, lactate, phosphonate, sulfonate, amino carboxylate, carboxylate, hydroxy carboxylate, organophosphate, organophosphonate, organosulfornate and organosuflate.

Polymers for use in the invention can be either heterogeneous mixtures of polymers of different "n" number or homogenous fractions comprising specified "n" numbers purified by standard purification methods. As indicated above the polymers may also be cyclic and in addition may be branched.

Preferred numbers for "n" include 2-250, 2-100, 2-80 and 2-50.

TABLE A

Examples of polymer analogues arising from formula 1a.

| Name | $L_1$ | $G_1$ | $L_2$ | $G_2$ |
|---|---|---|---|---|
| Polyhexamethylene biguanide (PHMB) | $(CH_2)_6$ | Biguanide | $(CH_2)_6$ | Biguanide |
| Polyethylene biguanide (PEB) | $(CH_2)_2$ | Biguanide | $(CH_2)_2$ | Biguanide |
| Polyethylenetetramethylene biguanide | $(CH_2)_2$ | Biguanide | $(CH_2)_4$ | Biguanide |
| Polyethylene hexamethylene biguanide (PEHMB) | $(CH_2)_2$ | Biguanide | $(CH_2)_6$ | Biguanide |
| Polypropylene biguanide, Polyaminopropyl biguanide (PAPB) | $(CH_2)_3$ | Biguanide | $(CH_2)_3$ | Biguanide |
| Poly-[2-(2-ethoxy)-ethoxyethyl]-biguanide-chloride] (PEEG) | $(CH_2CH_2OCH_2CH_2OCH_2CH_2)$ | Biguanide | $(CH_2CH_2OCH_2CH_2OCH_2CH_2)$ | Biguanide |
| Polypropylenehexamethylene biguanide | $(CH_2)_3$ | Biguanide | $(CH_2)_6$ | Biguanide |
| Polyethyleneoctamethylene biguanide | $(CH_2)_2$ | Biguanide | $(CH_2)_8$ | Biguanide |
| Polyethylenedecamethylene biguanide | $(CH_2)_2$ | Biguanide | $(CH_2)_{10}$ | Biguanide |
| Polyethylenedodecamethylene biguanide | $(CH_2)_2$ | Biguanide | $(CH_2)_{12}$ | Biguanide |
| Polytetramethylenehexamethylene biguanide | $(CH_2)_4$ | Biguanide | $(CH_2)_6$ | Biguanide |
| Polytetramethylenebiguanide | $(CH_2)_4$ | Biguanide | $(CH_2)_4$ | Biguanide |
| Polypropyleneoctamethylene biguanide | $(CH_2)_3$ | Biguanide | $(CH_2)_8$ | Biguanide |
| Polytetramethyleneoctamethylene Biguanide | $(CH_2)_4$ | Biguanide | $(CH_2)_8$ | Biguanide |
| Polyhexamethylene diethylenetriamine biguanide | $(CH_2)_6$ | Biguanide | $CH_2-CH_2-NH-CH_2-CH_2$ | Biguanide |
| Polyhexamethylene guanide (PHMG) | $(CH_2)_6$ | guanidine | $(CH_2)_6$ | guanidine |
| Polyethylene guanide | $(CH_2)_2$ | guanidine | $(CH_2)_2$ | guanidine |
| Polyethylenetetramethylene guanide | $(CH_2)_2$ | guanidine | $(CH_2)_4$ | guanidine |
| Polyethylene hexamethylene guanide | $(CH_2)_2$ | guanidine | $(CH_2)_6$ | guanidine |
| Polypropylene guanide, Polyaminopropyl guanide (PAPB) | $(CH_2)_3$ | guanidine | $(CH_2)_3$ | guanidine |
| Poly-[2-(2-ethoxy)-ethoxyethyl]-guanide | $(CH_2CH_2OCH_2CH_2OCH_2CH_2)$ | guanidine | $(CH_2CH_2OCH_2CH_2OCH_2CH_2)$ | guanidine |
| Polypropylenehexamethylene guanide | $(CH_2)_3$ | guanidine | $(CH_2)_6$ | guanidine |
| Polyethyleneoctamethylene guanide | $(CH_2)_2$ | guanidine | $(CH_2)_8$ | guanidine |
| Polyethylenedecamethylene guanide | $(CH_2)_2$ | guanidine | $(CH_2)_{10}$ | guanidine |
| Polyethylenedodecamethylene guanide | $(CH_2)_2$ | guanidine | $(CH_2)_{12}$ | guanidine |
| Polytetramethylenehexamethylene guanide | $(CH_2)_4$ | guanidine | $(CH_2)_6$ | guanidine |
| Polypropyleneoctamethylene guanide | $(CH_2)_3$ | guanidine | $(CH_2)_8$ | guanidine |
| Polytetramethylene guanide | $(CH_2)_4$ | guanidine | $(CH_2)_4$ | guanidine |
| Polyhexamethylene diethylenetriamine guanide | $(CH_2)_6$ | guanidine | $CH_2-CH_2-NH-CH_2-CH_2$ | guanidine |

TABLE B

| CAS numbers for example compounds arising from formula 1a | |
|---|---|
| Polymer | CAS Number |
| Polyhexamethylene biguanide hydrochloride (PHMB) | 27083-27-8 |
| | 32289-58-0 |
| Polyhexamethylene guanidine hydrochloride (PHMG) | 57028-96-3 |
| Poly-[2-(2-ethoxy)-ethoxyethyl]-guanidinium-chloride] (PEEG) | 374572-91-5 |

| Examples of polymer analogues arising from formula 1b. | | | | | |
|---|---|---|---|---|---|
| Name | $L_3$ | $G_4$ | $L_4$ | $G_5$ | x |
| Polyallylbiguanide | ($CH_2$—CH) | Biguanide | ($CH_2$—CH) | Biguanide | $CH_2$ |
| poly(allylbiguanidnio-co-allylamine) | ($CH_2$—CH) | amine | ($CH_2$—CH) | biguanide | $CH_2$ |
| poly(allylcarbamoylguanidino-co-allylamine) | ($CH_2$—CH) | amine | ($CH_2$—CH) | Carbamoyl guanidine | $CH_2$ |
| polyvinylbiguanide | ($CH_2$—CH) | Biguanide | ($CH_2$—CH) | biguanide | absent |

The polymer used in the method of the invention may comprise linear, branched or dendrimeric molecules. The polymer may comprise a combination of linear, branched or dendrimeric molecules. The polymer may comprise one or any combination of molecules of Formula 1a or Formula 1b, for example as described above.

For example, the polymer can comprise one or more of polyhexamethylene biguanide (PHMB), polyhexamethylene monoguanide (PHMG), polyethylene biguanide (PEB), polytetramethylene biguanide (PTMB) or polyethylene hexamethylene biguanide (PEHMB). Some examples are listed in table A and B.

Thus, the polymer may comprise homogeneous or heterogeneous mixtures of one or more of polyhexamethylene biguanide (PHMB), polyhexamethylene monoguanide (PHMG), polyethylene biguanide (PEB), polytetramethylene biguanide (PTMB), polyethylene hexamethylene biguanide (PEHMB), polymethylene biguanides (PMB), poly(allylbiguanidnio-co-allylamine), poly(N-vinylbiguanide), polyallybiguanide.

Most preferred the polymer comprises polyhexamethylene biguanide (PHMB).

The nanoparticles may be formed with and/or in the presence of the antifungal agent. Various methods may be used to form the nanoparticles and it is envisaged that the nanoparticles will be formed as a polymer and antifungal agent complex. However, polymer nanoparticles may be independently formed and then incubated with the antifungal agent so that it is absorbed or attached to the nanoparticles in such a way so as to retain their efficacy against the fungi.

In one embodiment of the present invention, a usually systemically administered antifungal agent is present in a dosage amount within the composition that is less than the therapeutically effective systemic dose of the antifungal agent. As the topical composition can more effectively administer the antifungal agent to the site of infection, the dosage can be reduced and this can reduce potential toxicological issues with some agents.

It will be apparent to the skilled addressee that the composition may further comprises one or more of the following component: buffers, excipients, binders, oils, water, emulsifiers, glycerin, antioxidants, preservatives and fragrances or any additional components usually found in topical creams and ointments. Furthermore, the composition could be in a number of forms such as a paste or a suspension for use with a spraying device or formulated for use in conjunction with a micro-needle array delivery system. If a micro-needle array is employed then it may be incorporated into an adhesive patch.

For certain applications, the composition may additionally comprise a permeating agent so as to allow delivery of the antifungal agent to infected area. For example, urea can be used to allow the nanoparticles breach the nail of an individual suffering from a fungal nail infection where the infection is underneath or in the nail itself.

The composition of the invention may also be administered intranasally or by inhalation and may be conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the composition, e.g. using a mixture of ethanol and the propellant as the solvent, which may additionally contain a lubricant, eg sorbitan trioleate. Capsules and cartridges (made, for example, from gelatin) for use in an inhaler or insufflator may be formulated to contain a powder mix of the composition of the invention and a suitable powder base such as lactose or starch.

Aerosol or dry powder formulations are preferably arranged so that each metered dose or "puff" contains at least 1 μg of the composition for delivery to the patient. It will be appreciated that the overall daily dose with an aerosol will vary from patient to patient, and may be administered in a single dose or, more usually, in divided doses throughout the day.

Alternatively, the composition of the invention can be administered in the form of a suppository or pessary, or they may be applied topically in the form of a lotion, solution, cream, ointment or dusting powder. The composition of the invention may also be transdermally administered, for example, by the use of a skin patch. They may also be administered by the ocular route, particularly for treating diseases of the eye.

For ophthalmic use, the composition of the invention can be formulated using nanoparticle systems or as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the composition of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The topical composition as herein above described can be used to treat a number of fungal infections. However, it is particularly suited to treat fungal nail infection, athlete's foot or other types of fungal skin infection/dermatophyte infections (such as ringworm of the groin (Tinea cruris), ringworm of the body (Tinea corporis), ringworm of the scalp (Tinea capitis), other "ringworm" type infections). The invention will also be suited to treating yeast infections such as, but not limited to, intertrigo, *pityriasis versicolor*, and thrush (*Candida albicans*).

The antifungal agent employed will of course be largely governed by its efficacy against the fungi causing the infection. The antifungal agent may comprise one or more agents selected from the following group: Nystatin, Terbinafine, Ketoconazole, Amphotericin B, Itraconazole or Berberine.

The fungal infection may comprise a dermatophytic infection. However, the present invention can also be used to treat yeast infections and/or colonisation.

In a further aspect of the present invention, there is provided a topical medicament comprising a nanoparticulate combination of polyhexamethylene biguanide and an antifungal agent for the treatment of a fungal infection.

In accordance with a further aspect of the present invention, there is provided the use of polyhexamethylene biguanide (PHMB) to form one or more nanoparticles with, or associated with, an antifungal agent in the preparation of a topical medicament. The nanoparticles will be used as the delivery vehicle for the antifungal agent to an infected area and also forms a synergistic effect when treating fungus infections. It will be apparent to the skilled addressee that the use of PHMB will be to form a composition as herein above described with reference to the first aspect of the invention.

In accordance with a yet further aspect of the present invention, there is provided a method of producing a topical composition for the treatment of a fungal infection comprising mixing a polymer capable of forming nanoparticles with an antifungal agent under conditions suitable to allow the formation of nanoparticles. Again, it will be apparent that the method will be employed to produce a composition as herein above described.

In a yet an additional aspect of the present invention, there is provided a combination of a composition comprising a polymer capable of forming nanoparticles and an antifungal agent and a micro-needle array for use in the treatment of a fungal nail infection. The micro-needle array may be incorporated into an adhesive patch. The micro-needles may be less than 2 mm in length. More preferably, the micro-needles are less than 1.5 mm in length. Most preferably, the micro-needles are less than 1 mm in length. Preferably, less than 500 µm of the micro-needles are inserted into the skin. More preferably, less than 400 µm of the micro-needles are inserted into the skin. Most preferably, about 300-200 µm of the micro-needs are inserted into the skin. Preferably, the micro-needles administer the composition to the dermis and/or epidermis.

DETAILED DESCRIPTION OF THE INVENTION

Embodiments of the present invention will now be described, by way of example only, with reference to the following experiments and accompanying figures, in which:

FIG. 1 is a graph showing the reduction in Minimum Inhibitory Concentration (MIC) of antifungals against *Saccharomyces cerevisiae* EBY100, when combined with PHMB. Filled squares represent MIC of drug alone and filled circles represent MIC of drug when combined with PHMB. Fold reduction in MIC of each drug is: nystatin—2 fold, amphotericin B—4 fold, berberine—2 fold, ketoconazole—4 fold and terbinafine—8 fold;

FIG. 2 is a graph showing the MIC of antifungals against *Saccharomyces cerevisiae* NOD 24, when combined with PHMB. Filled squares represent MIC of drug alone and filled circles represent MIC of drug when combined with PHMB. Fold reduction in MIC of each drug is: nystatin—4 fold, amphotericin B—16 fold, berberine—16 fold, ketoconazole—4 fold and terbinafine—16 fold;

FIG. 3 is a graph showing the reduction in MIC of antifungals against *Candida albicans*, when combined with PHMB. Filled squares represent MIC of drug alone and filled circles represent MIC of drug when combined with PHMB. Fold reduction in MIC of each drug is: nystatin—2 fold, amphotericin B—2 fold, berberine—2 fold, ketoconazole—4 fold and terbinafine—4 fold;

FIGS. 4A-4E are graphs showing the changes in fluorescence/absorbance of antifungal agents when combined with PHMB. Changes in fluorescence emission intensity of fluorescent compounds in presence and absence of PHMB was tested. Fluorescence of ketoconazole (FIG. 4A), amphotericin B (FIG. 4B), berberine (FIG. 4C) and nystatin (FIG. 4D) was decreased (fluorescence quenching). Changes in Absorbance of terbinafine in presence and absence of PHMB was tested and found to be increased (hyperchromic effect) (FIG. 4E);

FIGS. 5 (*a*) and (*b*) are graphs showing the size distribution of particles formed tested using Dynamic light scattering. FIG. 5 (*a*) shows the size distribution of particles (Average size=22.22±1.591 nm) formed when Berberine was combined with PHMB in the ratio 1:3, whereas FIG. 5 (*b*) shows the size distribution of particles formed when Ketoconazole was combined with PHMB in the ratio 1:3. Peak 1 Average size=1.15±0.017, Peak 2 Average size=5.88±0.71 and Peak 3 Average size=498.9±65.2;

FIG. 6 shows fluorescence microscopy images of *C albicans* showing enhanced delivery of Berberine when combined with PHMB. A=Untreated *C albicans* stained with DAPI hence nucleus is blue. B=*C albicans* treated with 1 µg/ml of berberine alone showing green fluorescence inside the cytoplasm due to delivery of small amount of berberine. C=*C albicans* treated with 1 µg/ml of berberine and 1.25 µg/ml of PHMB showing enhanced green fluorescence of cytoplasm indicating increased delivery of berberine. Bar=5 µm;

FIG. 7 is a graph showing the flow cytometry analysis of Berberine positive *C albicans* cells when treated with Berberine alone and with combination of Berberine and PHMB.

% of cells are represented as mean of triplicates±SD. This figure indicates as the concentration of PHMB increases from 1.25 to 5 μg/ml there is an increase in delivery into cells. For each concentration of Berberine, the columns are as follows: Berberine alone, 1.25 μg/ml PHMB; 2.5 μg/ml PHMB; and 5 μg/ml PHMB;

an antifungal agent and PHMB would enable a reduction in dose of drug thus reduction in toxicity and/or increase internalisation of drug the agent and if there was any synergistic effect.

The experiments focussed on antifungals which have intracellular targets for antifungal action and are currently used in clinics but less preferred because of solubility issues, toxicity and resistance. Along with clinically used antifungals a novel candidate, Berberine, with proven in vitro antifungal activity was also studied (Zhao et al., (2010) *J. Therm. Analysis and Calorimetry*, 102, 49-55). The selected candidates are illustrated below in Table 1.

TABLE 1

| Drugs | Class | Mechanism of action | Reasons for selection | Current uses |
|---|---|---|---|---|
| Nystatin | Polyene | Binding to ergosterol and causing perturbing in the cell membrane there by causing leakage of cellular contents | Intracellular action and toxicity at higher doses | *Candida albicans* infections, adjunct in the treatment of dermatitis |
| Amphotericin B | | | Intracellular action, resistance, toxicity at higher doses and high molecular mass preventing skin penetration | Systemic fungal infections, skin infections by *Candida* sp |
| Terbinafine | Allyl amine | | Intracellular action, less effective against common yeast hence used in combination with azoles (Kontoyiannis and Lewis, 2002) | Fungal infections in dogs that affect either the claws on the front or the rear paws, used against *Malassezia* sp and dermatophyte infections |
| Ketoconazole | Azole | Inhibits cytochrome P450 enzyme 14-α-sterol-demethylase | Intracellular action, resistance and high molecular mass preventing skin penetration | Systemic treatment of otitis and against *Malassezia* sp *Candida* sp *Microsporum canis* and Aspergillosis |
| Berberine | Alkaloid | Unknown | Intracellular action, potential novel candidate as antifungal | Not used clinically as an antifungal |

Figure 10:
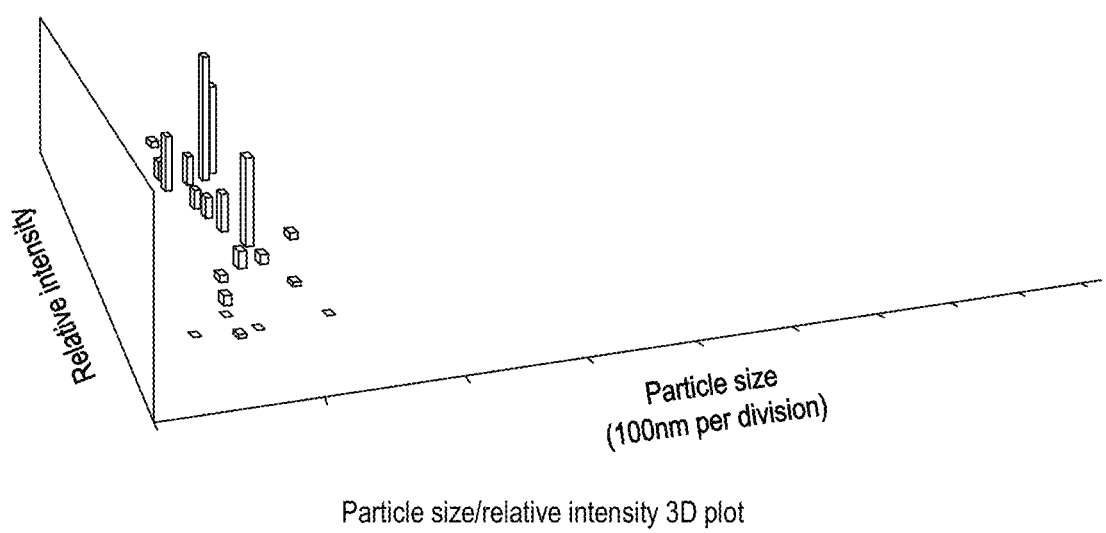
Figure 11:
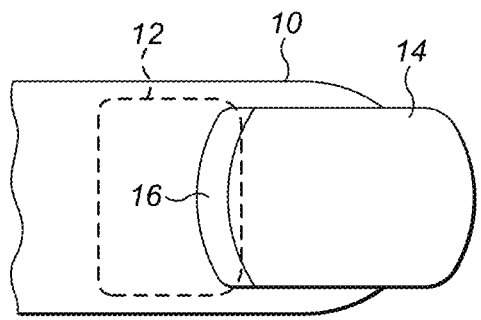
Figure 12:
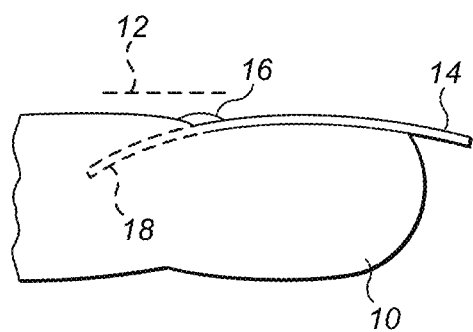

FIG. 10 is a graph showing the nanoparticle size/relative intensity 3D plot of nanoparticles produced comprising Terbinafine and PHMB;

FIG. 11 is a plan view diagram of a finger with a nail which is to be treated with a micro-needle patch for delivering the composition of the present invention;

FIG. 12 is a cross-sectional diagram of a finger as shown in FIG. 11; and

Figure 13:
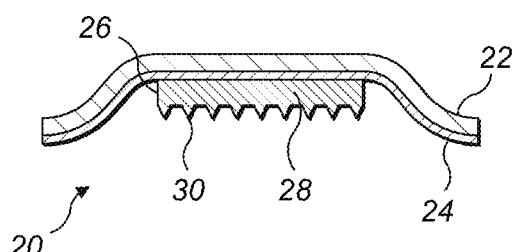

FIG. 13 is a cross-sectional diagram of a micro-needle patch.

The aim of the following experiments were to investigate whether cellular delivery of antifungals could be enhanced using a nanotechnology based delivery system with a cationic polymer Polyhexamethylene Biguanide (PHMB). The experiments also explored a new strategy of combining antifungals with PHMB which can form nanoparticles with small molecules. PHMB is an inexpensive, readily available disinfectant and antiseptic used commonly in dressings, swimming pools and contact lens solutions. It is believed that its antiseptic action works by disrupting cell membranes of organisms and thereby causing leakage of cell contents. The experiments also assessed whether the combination of In vitro susceptibility of a clinical isolate of *Candida albicans*, *Saccharomyces cerevisiae* NOD 24 and *S cerevisiae* EBY 100 to the combination of the antifungal agent and PHMB was assessed using chequerboard assay. Interaction between the drugs and PHMB, formation of nanoparticles and cellular uptake was also assessed.

Antifungals

Nystatin, terbinafine, ketoconazole and berberine were obtained as powder from Sigma-Aldrich, UK. Amphotericin B was obtained from Sigma as solution in deionised water. Dimethyl sulfoxide (DMSO) was also from Sigma. Stock solutions of nystatin (5 mg/ml), terbinafine (15 mg/ml), ketoconazole (5 mg/ml) and amphotericin B (0.2 mg/ml) were prepared in DMSO. Berberine was dissolved in water to make stock solution of 10 mg/ml. PHMB stock (5 mg/ml) was also made in water. All the stock solutions were made into different aliquots of 500 μl, kept at −20° C. and protected from light.

Strains

Two strains of *Saccharomyces cerevisiae* and one clinical isolate of *Candida albicans* were studied. *S cerevisiae* NOD 24 was obtained from Royal Veterinary College and *S*

*cerevisiae* EBY 100 from Allinson Bread®, UK. The clinical isolate of *C albicans* was also obtained from Royal Veterinary College.

Media

RPMI 1640 medium was obtained as powder and dissolved in distilled water and buffered with 0.165M morpholino propanesulfonic acid (MOPS) according to standard procedure. The pH was adjusted to 7 using 1M sodium hydroxide solution. Sabouraud's Glucose Agar (SGA) was obtained as powder. All media and chemicals were from Sigma-Aldrich, UK.

Inoculum Preparation

Yeast inoculum was prepared by picking five colonies from 24 hrs grown culture in SGA and mixing in RPMI 1640 with MOPS. The optical density of the mixture was adjusted spectrophotometrically to 1 which is equivalent to $3\times10^7$ Colony Forming Units of yeast/ml. This suspension was further diluted in RPMI 1640 with MOPS to give final inoculum size of $0.5\times10^4$ CFU/ml.

Chequerboard Titration Test

Chequer board titration test was carried out in sterile 96-well plates as per CLSI recommended standard procedure to test the antifungal effect of drugs alone and in combination with PHMB. RPMI 1640 medium buffered with MOPS was used as test medium. Dilutions of drug was prepared the test medium if the stock was made in DMSO and in case of stocks made in water further dilutions of drug was in water itself. Tested concentrations were: nystatin 0.000039 mg/ml to 0.02 mg/ml, amphotericin B 0.032 mg/ml to 0.0000625 mg/ml, berberine 0.01 mg/ml to 0.00002 mg/ml, ketoconazole 0.032 mg/ml to 0.0000625 mg/ml and terbinafine 0.16 mg/ml to 0.00031 mg/ml. Growth control and sterility control was present in all plates. All the plates were prepared in triplicates.

Incubation and Calculation of Minimum Inhibitory Concentration (MIC) and Fractional Inhibitory Concentration Index (FICI)

The plates were sealed with paraffin foil to prevent evaporation and kept at 37° C. for *C albicans* and 30° C. for *S cererevisiae*. MIC was recorded visually, aided with Powerwave 340 universal microplate spectrophotometer (Biotek) after 24 hours for *C albicans* and *S cerevisiae* NOD 24. But it was recorded after 48 hours for *S cerevisiae* EBY 100 as there was no growth even in growth control wells after 24 hrs. MIC was defined as the lowest concentration at which there is no visible growth. FICI was used to analyse the drug interactions in vitro and was calculated using the equation given below:

$$FICI = \frac{MIC \text{ of drug in combination}}{MIC \text{ of drug alone}} + \frac{MIC \text{ of PHMB in combination}}{MIC \text{ of PHMB alone}}$$

FICI values were interpreted according to recommended standards (FICI≤0.5 is 'synergistic effect', >0.5 but ≤4 is 'no interaction' and >4 is 'antagonistic effect').

Fluorescence and Absorbance Studies

Interaction of fluorescent antifungals with PHMB was tested flourometrically. A specific concentration of each drug was allowed to interact with different concentrations of PHMB and changes in the fluorescence intensity were studied. The experiment was carried out in 96 well flat bottom quartz plates. 150 µg/ml berberine, 5 µg/ml ketoconazole and 5 µg/ml amphotericin B mixed with PHMB in w/w ratios 1:0 to 1:10. 50 µg/ml nystatin was mixed with PHMB in w/w ratios 1:0 to 1:4. In the case of terbinafine which is not fluorescent, changes in absorbance were studied. 10 µg/ml Terbinafine was mixed with PHMB in w/w ratios 1:0 to 1:5. Solutions were prepared from stocks in phosphate buffered saline (PBS) for all drugs except for Berberine for which water was used as it precipitated in PBS at the concentration. The mixture was thoroughly mixed by pipetting and was kept at room temperature for 20 minutes and then tested for change in fluorescence/absorbance. Fluorescence was tested in Infinite M200 Pro Fluorometer (Tecan). To test the fluorescence intensity excitation and emission wavelength were 320 nm and 410 nm for nystatin, 340 nm and 480 nm for amphotericin B, 350 nm and 550 nm for berberine, 260 nm and 375 nm for ketoconazole respectively. In the case of Terbinafine, changes in absorbance were studied using ND1000 spectrophotometer (Nanodrop). The absorbance peak for terbinafine was at 272 nm. Changes in maximum absorbance at 272 nm were plotted against the concentration of PHMB.

Particle Formation and Determination of Particle Size

Dynamic light scattering (DLS) was used to estimate size of complexes formed. It is based on the principle that by measuring scattered light from particles in motion their size can be determined. Antifungals (100 µg/ml) and PHMB were thoroughly mixed in w/w ratio 1:3 in PBS and kept for 20 minute at room temperature. Particle size was determined using Zetasizer S (Malvern instruments, UK).

Microscopy

The cellular delivery of berberine was visually detected as the compound is fluorescent enough to be detected by microscopy. *C albicans* cells were treated with berberine alone and also with combinations of berberine and PHMB. 50 µl of 1 µg/ml, 2 µg/ml and 3 µg/ml of Berberine solutions were mixed properly with 50 µl of 1 µg/ml and 2.5 µg/ml of PHMB in sterile 96 well plates by pipetting 3-4 times and was kept at room temperature for 20 minutes. 100 µl of *C albicans* cells in RPMI 1640 was added to these wells, to 100 µl of Berberine alone solutions and to 100 µl of PBS and kept at 37° C. for 1 hour. Contents of each well were transferred to eppendorf tubes and centrifuged at 5000 rpm for 10 minutes. After removing supernatant, 100 µl of 2.5 µg/ml 4', 6' diamino-2-phenylindole (DAPI) was added to each tube to stain nucleus of fungi. Slides were prepared in agarose bed and observed under DM4000 upright fluorescence microscope (Leica microsystems) using oil immersion lens.

Flow Cytometry

Cellular delivery of berberine into *C albicans* when combined with PHMB was tested quantitatively using flow cytometry. In a 96 well plate yeast cells were treated with 1 µg/ml-5 µg/ml of berberine alone and combinations of these concentrations with 1.25, 2.5, 5 µg/ml of PHMB. The procedure was exactly same as the one for microscopy. After centrifugation 100 µl of supernatant was removed was 400 µl of PBS was added and was tested for delivery of berberine using FITC (fluorescein isothiocyanate) filter in FACS Canto™ II Flow cytometer (BD Biosciences). Data was acquired using FACS Diva software and analysed using Flowjo 5.6.5 software.

Statistical Analysis

Wilcoxon signed rank test was used to statistically analyse changes in MICs of antifungals when combined with PHMB. P value less than 0.05 was considered significant. Statistical analysis was done using SPPSS version 2.0 software.

Chequer Board Assay

The susceptibility of fungi to selected antifungals and their combination with PHMB chequerboard assay was measured by assessing the changes in MICs of antifungals to know whether there is any reduction when PHMB and drugs are acting together. All the drugs showed a significant reduction in MIC when combined with PHMB (p value=0.043). MICs of antifungals and FICI values are summarised in Table 2 below.

TABLE 2

| Organism | Antifungals | MIC of antifungals alone (mg/ml) | MIC when combined with PHMB (mg/ml) | FICI | Type of interaction |
|---|---|---|---|---|---|
| Saccharomyces cerevisiae NOD 24 | PHMB | 0.001 | — | — | — |
| | Nystatin | 0.0025 | 0.000625 | 0.75 | No interaction |
| | Amphotericin B | 0.004 | 0.00025 | 0.56 | No interaction |
| | Berberine | 0.05 | 0.00056 | 0.56 | No interaction |
| | Ketoconazole | 0.016 | 0.001 | 0.5 | Synergistic |
| | Terbinafine | 0.004 | 0.0025 | 0.312 | Synergistic |
| Saccharomyces cerevisiae EBY 100 | PHMB | 0.002 | — | — | — |
| | Nystatin | 0.005 | 0.0025 | 0.53 | No interaction |
| | Amphotericin B | 0.016 | 0.004 | 0.5 | Synergistic |
| | Berberine | 0.05 | 0.025 | 0.75 | No interaction |
| | Ketoconazole | 0.00125 | 0.00031 | 0.263 | Synergistic |
| | Terbinafine | 0.02 | 0.0025 | 0.14 | Synergistic |
| Candida albicans | PHMB | 0.001 | — | — | — |
| | Nystatin | 0.005 | 0.0025 | 1 | No interaction |
| | Amphotericin B | 0.001 | 0.0005 | 0.53 | No interaction |
| | Berberine | 0.062.5 | 0.03125 | 0.53 | No interaction |
| | Ketoconazole | 0.004 | 0.001 | 0.281 | Synergistic |
| | Terbinafine | 0.004 | 0.001 | 0.5 | Synergistic |

Figure 1:
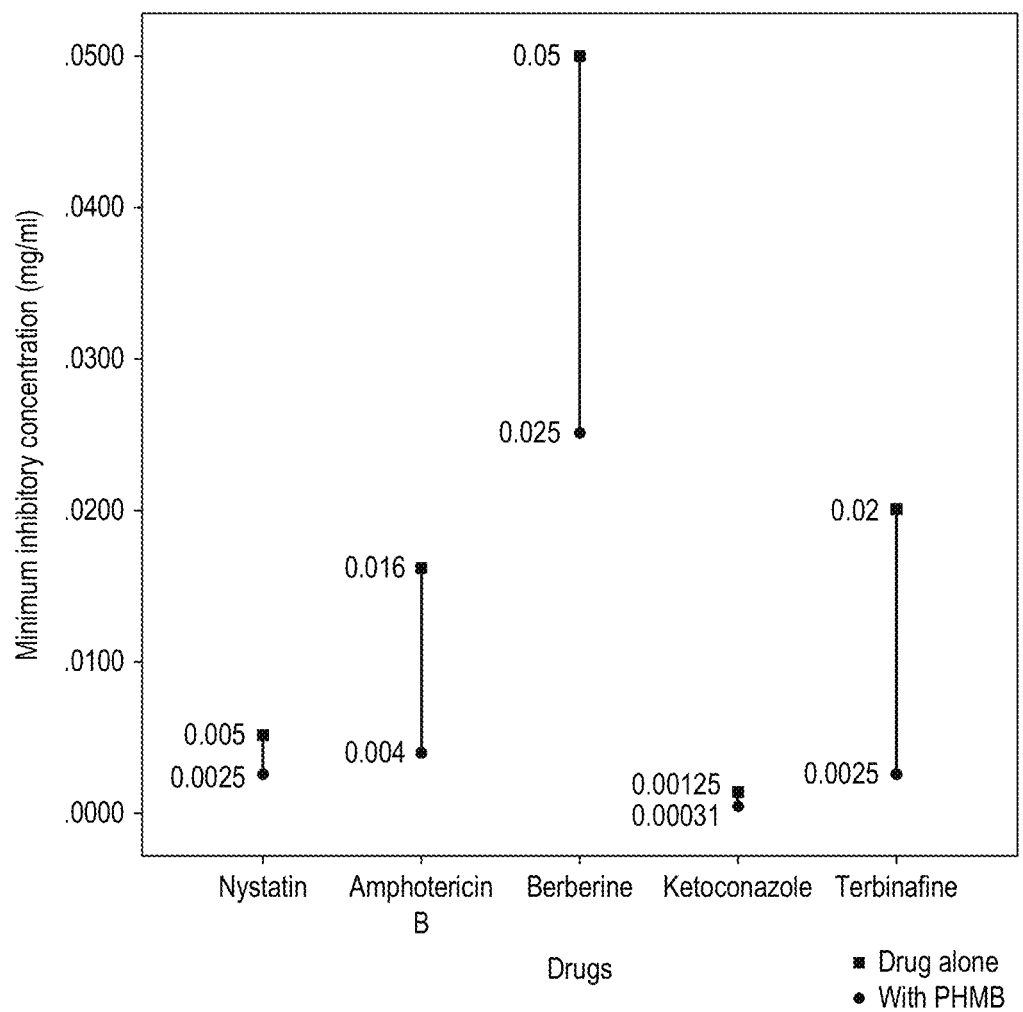
Figure 2:
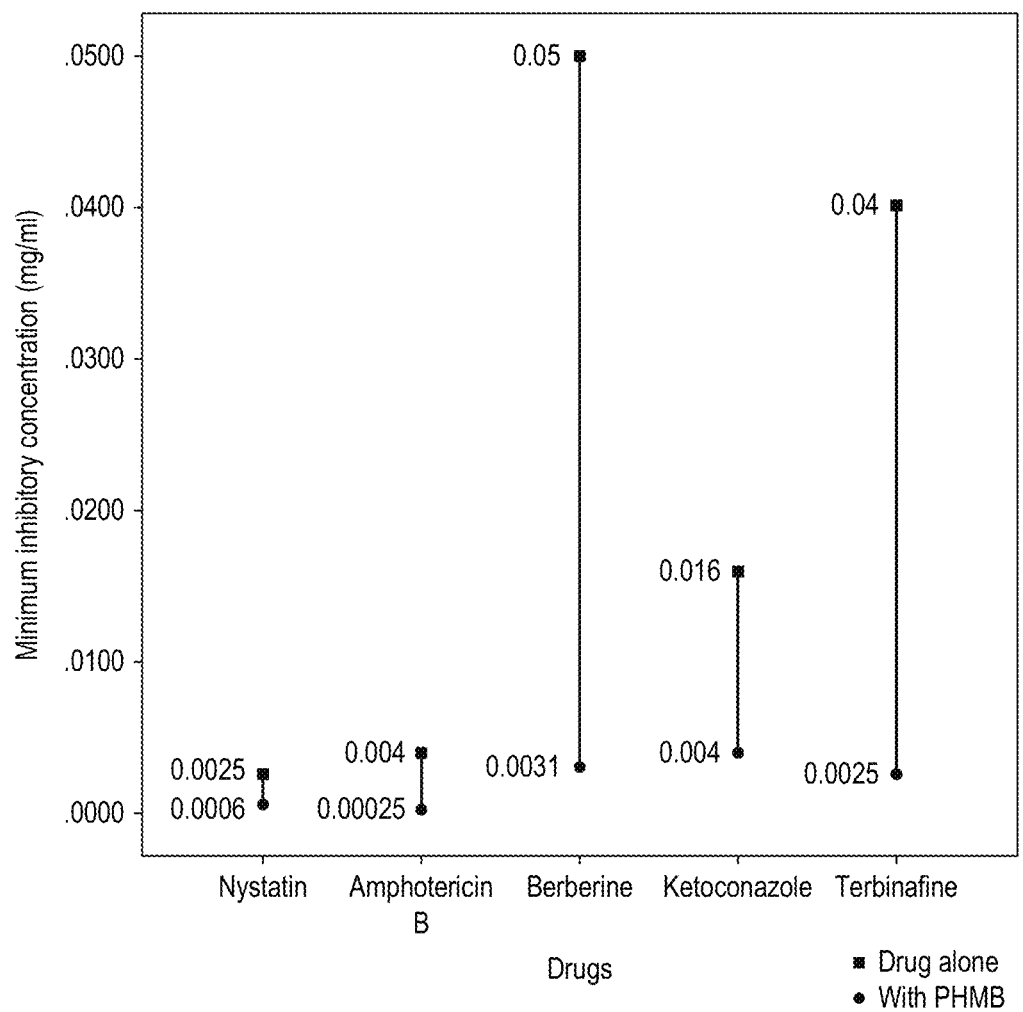
Figure 3:
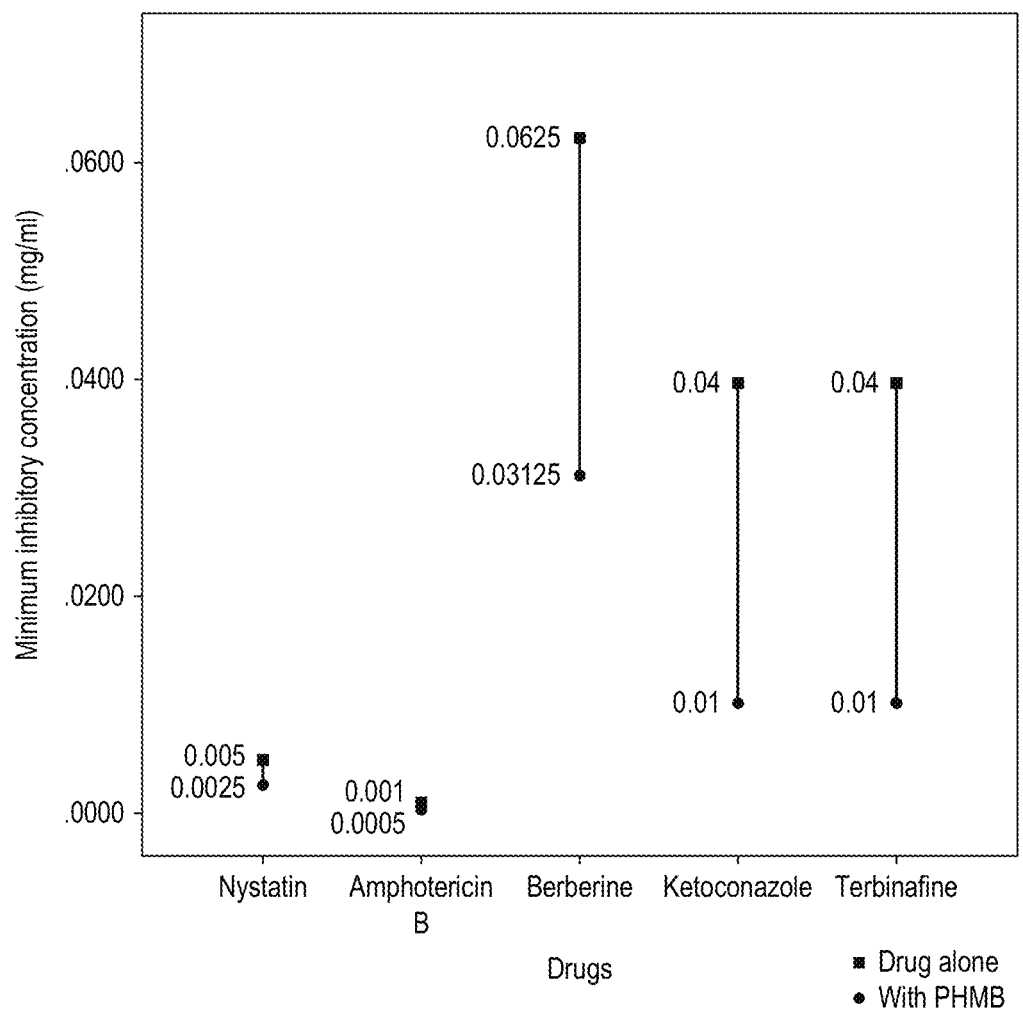
Figure 4A:
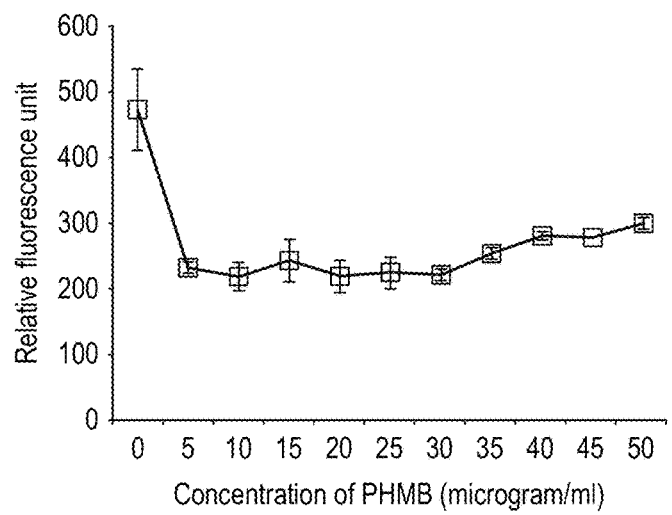
Figure 4B:
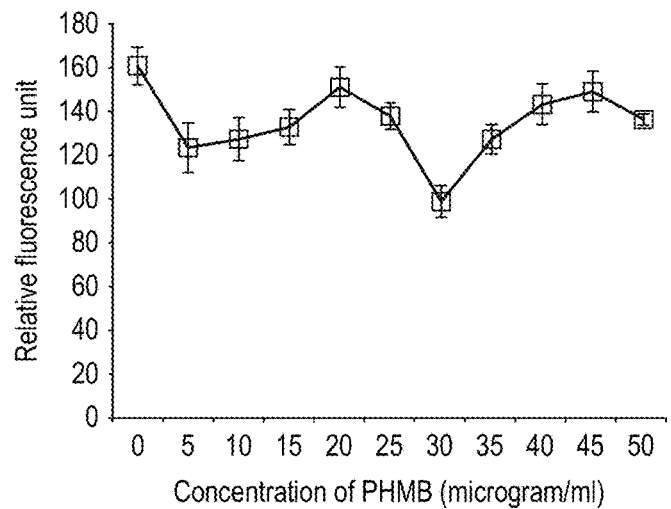
Figure 4C:
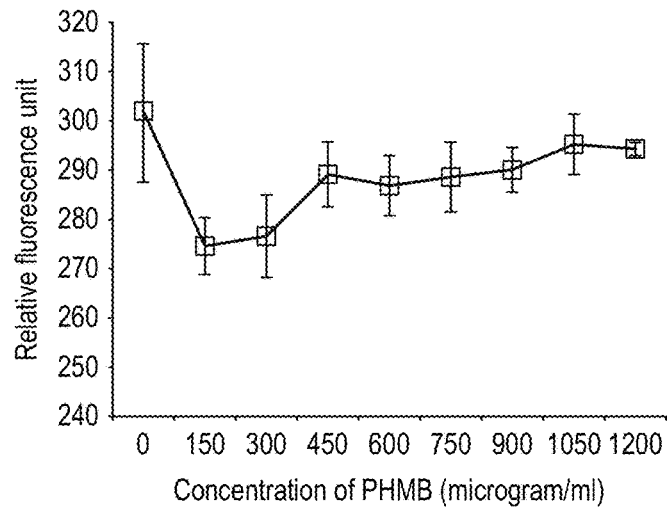
Figure 4D:
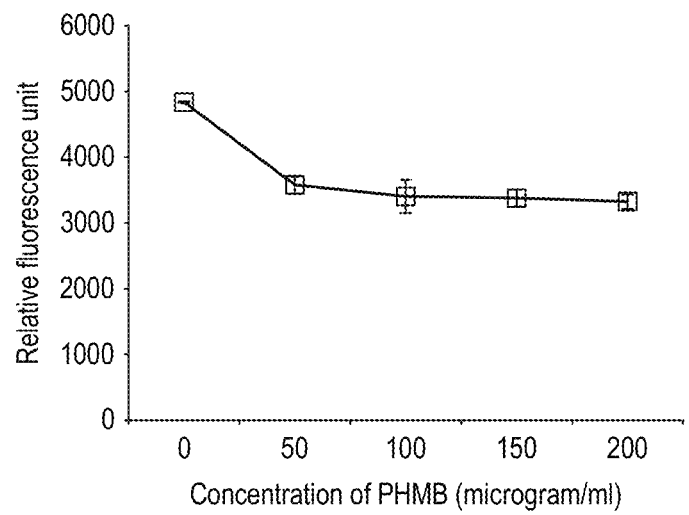
Figure 4E:
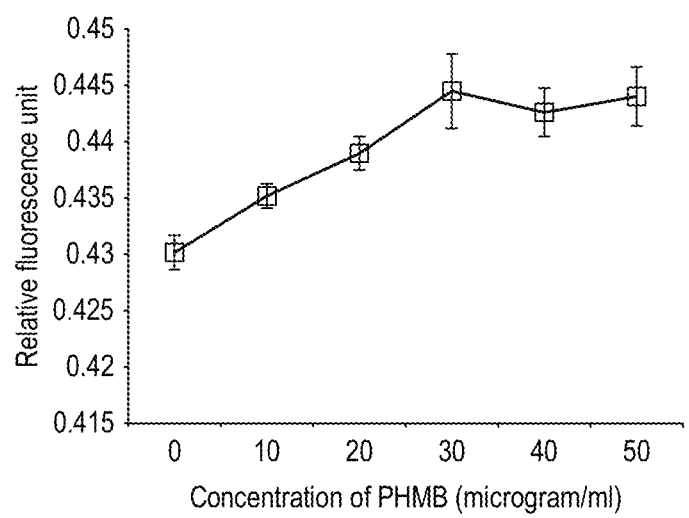

The drop in MICs is shown in FIGS. 1 to 3. All the drugs showed drop in MICs against all the organisms in combination with less than 0.00005 mg/ml of PHMB. Also there was significant (p value=0.045) decrease in MICs of PHMB when combined with antifungals which is illustrated in Table 3 below.

TABLE 3

| Organism | MIC of PHMB (mg/ml) | Drugs | MIC of PHMB with antifungals (mg/ml) |
|---|---|---|---|
| Saccharomyces cerevisiae NOD 24 | 0.001 | Nystatin | 0.0005 |
| | | Amphotericin B | 0.0005 |
| | | Berberine | 0.0005 |
| | | Ketoconazole | 0.0005 |
| | | Terbinafine | 0.000062 |
| Saccharomyces cerevisiae EBY 100 | 0.002 | Nystatin | 0.000062 |
| | | Amphotericin B | 0.0005 |
| | | Berberine | 0.0005 |
| | | Ketoconazole | 0.000031 |
| | | Terbinafine | 0.000031 |
| Candida albicans | 0.001 | Nystatin | 0.0005 |
| | | Amphotericin B | 0.000031 |
| | | Berberine | 0.000031 |
| | | Ketoconazole | 0.000062 |
| | | Terbinafine | 0.0005 |

During chequerboard assay we encountered solubility problems with terbinafine in the medium. But this was solved by keeping it at 37° C. for 10 minutes. Some of antifungals showed synergy. There was difference in MICs of different drugs against different organisms as expected. Huge drops in MICs of antifungals against S cerevisiae NOD 24 was observed. Strong synergism with PHMB was found in case of terbinafine and ketoconazole. In the case of amphotericin B synergy was observed when tested against S cerevisiae EBY 100. The results from chequerboard assay indicate that PHMB can potentiate action of these antifungals Fluorescence and Absorbance Studies Interaction between PHMB and antifungals was tested by studying changes in their fluorescence intensity. The results are depicted in FIG. 4. There was decrease in fluorescence of all the compounds. At 1:6 ratio between ketoconazole and PHMB its fluorescence was dropped to almost 50%. Fluorescence of nystatin showed only a small decrease. During the study berberine was found to precipitate in PBS hence water was used as solvent. There was drop in fluorescence of berberine but then it started to slightly increase but it was never more than the sample with berberine alone. Similar was the observation with amphotericin B. This drop in fluorescence of sample is called fluorescence quenching. In case of terbinafine absorbance was found to increase slightly. This is called hyperchromic effect. Fluorescence quenching and hyperchromic effect shows that PHMB interacts with antifungals.

Size of Particles Formed

Figure 5A:
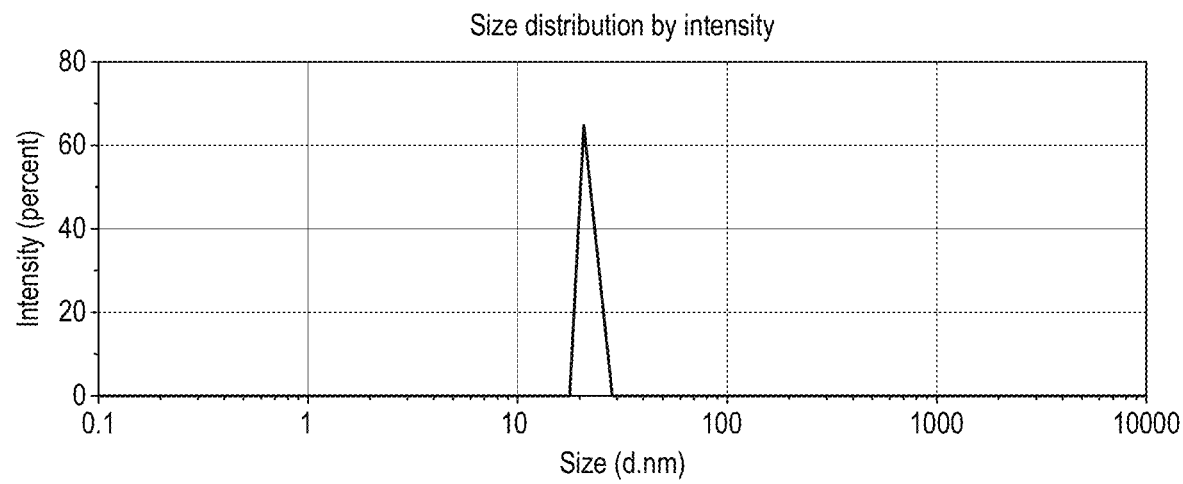
Figure 5B:
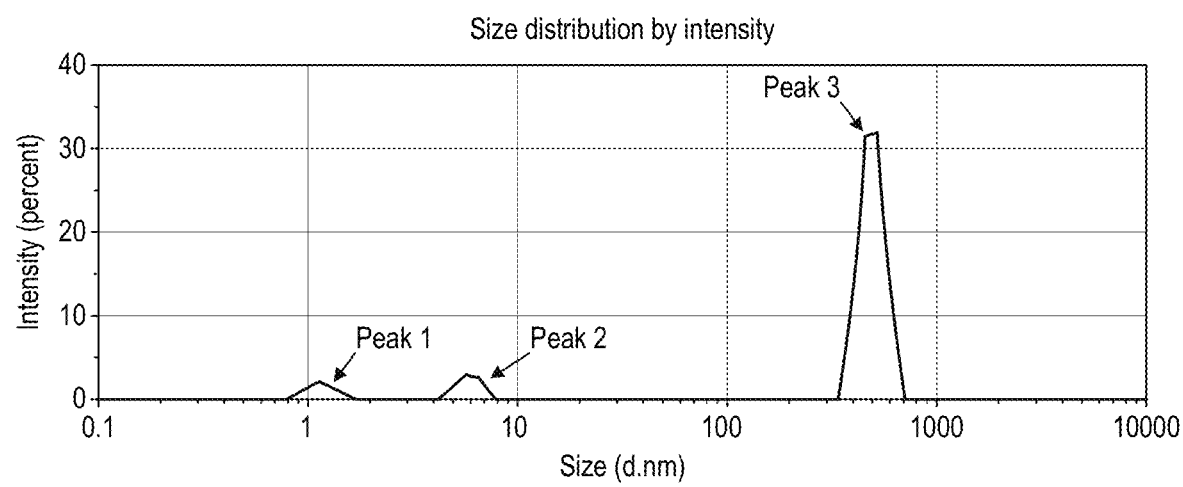

Size of the complexes formed between PHMB and antifungals was determined using DLS. Nanoparticles were observed in case of ketoconazole and berberine (FIG. 5). But in the case of ketoconazole, there were several larger sized particles also. In the case of berberine (FIG. 5 (a)) 64.5% of particles was around 22.2±1.5 nm. But for ketoconazole (FIG. 5 (b)) only less than 10% of particles were of size less that 10 nm. The polydispersity index was more than one 1, meaning wider particle size distribution. In the case of other drugs, particles from 50 to ≤1000 nm were observed. The results show that PHMB forms particles with all antifungals and nanoparticles with terbinafine, ketoconazole and berberine.

Microscopy

Figure 6A:
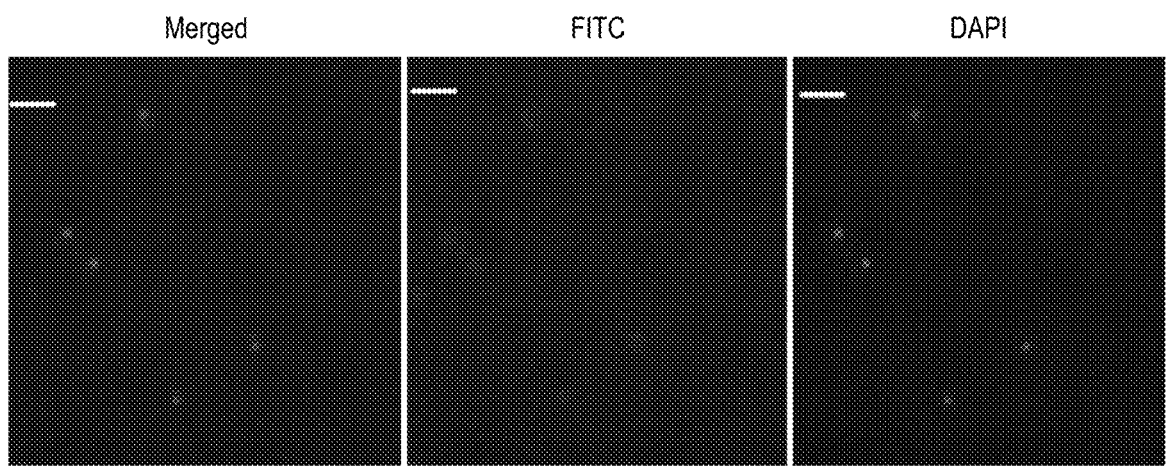
Figure 6B:
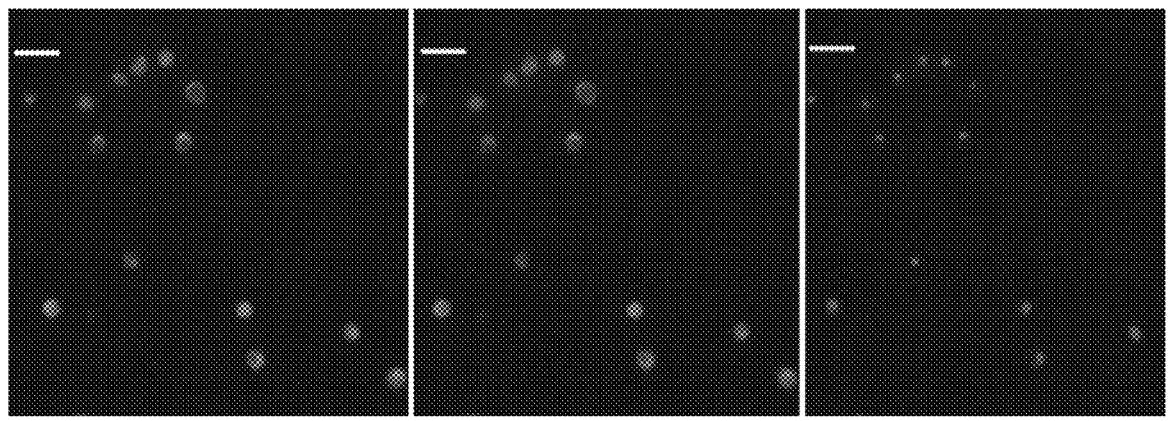
Figure 6C:
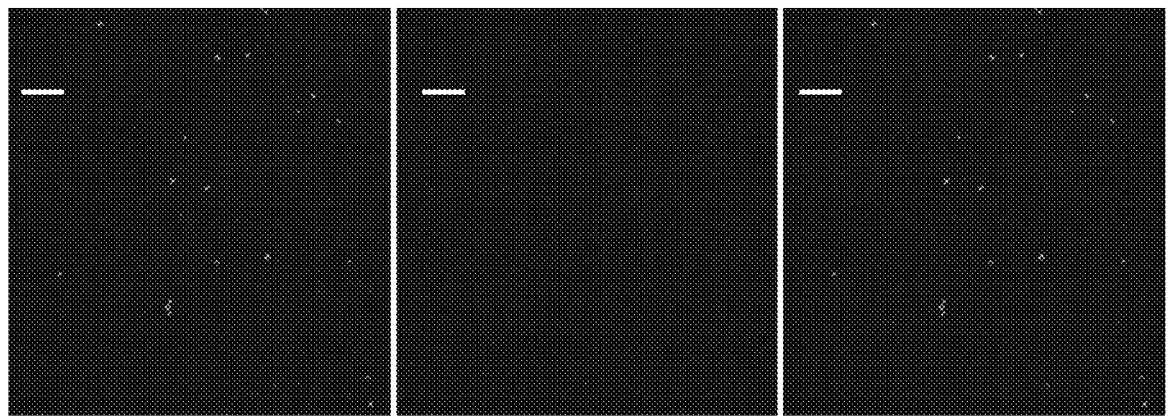

Cellular delivery of berberine into C albicans was tested using fluorescence microscopy. There was considerable increase in fluorescence of cells when berberine was combined with PHMB, compared with berberine alone as depicted in FIG. 6. Also increase in fluorescence was observed when concentration of PHMB was increased for the same concentration of berberine. FIG. 6 represents only one berberine concentration but similar results were observed for all the concentration studied. Results indicate that on addition of PHMB there is increase in entry of berberine into the cells compared to berberine alone. This qualitatively proves that PHMB can enhance delivery of berberine into fungi.

Flow Cytometry

Figure 7:
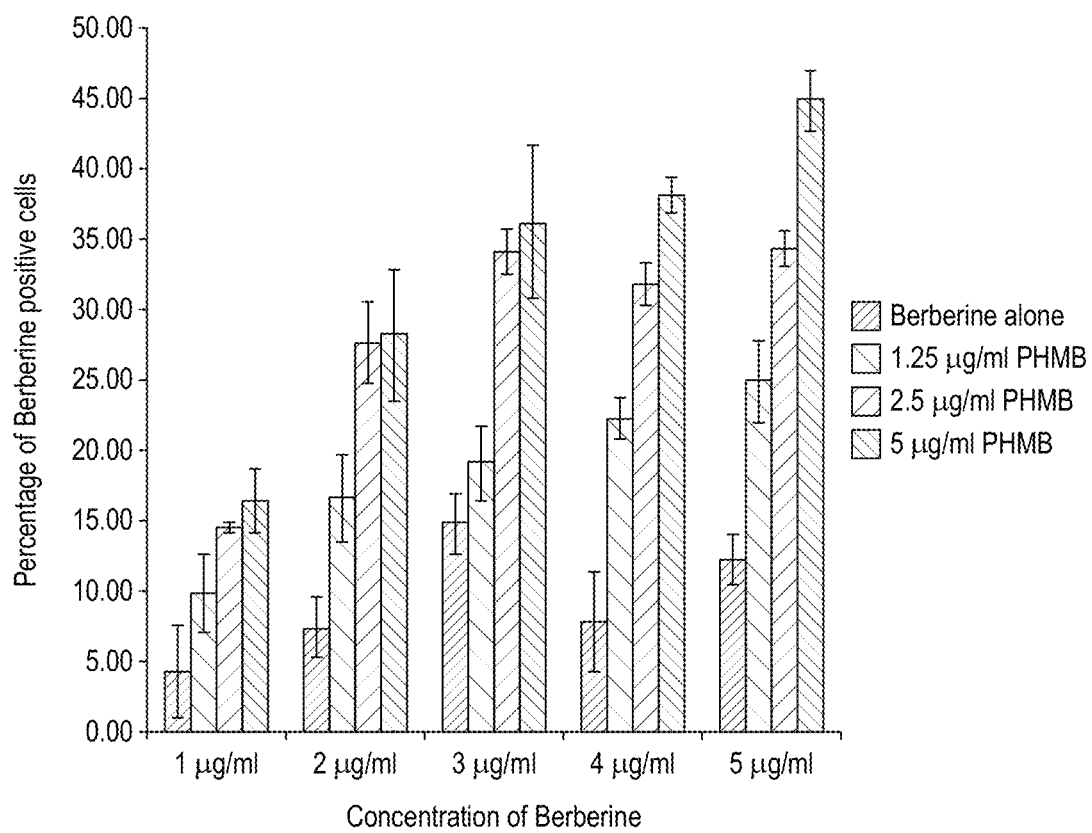

The enhanced delivery of berberine into *C albicans* was quantified using flow cytometry. FITC filter was used as the emission peak of berberine comes within FITC's absorption spectrum. There was a clear increase in number of cells positive for berberine when it was combined with PHMB as depicted in FIG. 7. The observation was similar to microscopy i.e., increase in berberine positive cells with increase in concentration of PHMB. A slight increase was observed with higher concentration of berberine alone also. These results indicate that PHMB increases cellular delivery of berberine into *C albicans*.

Results

PHMB is a low toxic, clinically safe antiseptic and the experiments show an enhanced delivery of antifungals by combining them with this cationic polymer. The drugs were tested for changes in their antifungal activity against *C albicans* and *S cerevisiae* when combined with PHMB. Interaction between the polymer and drugs was tested using fluorescence/absorbance studies and dynamic light scattering. Cell delivery of berberine was studied using flow cytometry and fluorescence microscopy.

The experiments show that there is significant reduction (p value=0.043) in MICs of all drugs when combined with PHMB. Also fluorescence intensity and absorbance of all drugs studied were altered in the presence of PHMB indicating interaction. Drug—PHMB interactions were confirmed by dynamic light scattering. Nanoparticles were observed in the case of berberine, terbinafine and ketoconazole. Increased cellular delivery of berberine into *C albicans* was visualised using microscopy and quantified through flow cytometry.

PHMB potentiates action of antifungals, forms nanoparticles and enhance cellular delivery of berberine and it is envisaged that the use of nanoparticles in combination with and antifungal agents will improve antifungal activities in vivo.

PHMB enhanced antifungal action of all the drugs studied as there was decrease in MICs of all the drugs which is illustrated in Table 2. Synergistic effect was observed for ketoconazole, terbinafine and amphotericin B.

It was hypothesised that PHMB forms nanoparticles with the selected antifungals. Nanoparticles were not detected when nystatin, terbinafine and amphotericin B were combined with PHMB in the ratio 1:3. Larger sized particles within size range of 500 to 1000 nm were detected. This could be due to aggregation or precipitation. However, it is believed that combining the drugs and PHMB in different ratios would result in nanoparticle formation in addition to altering the temperature at which particles are formed, changing the medium/solvent of reaction and adjusting the pH.

The alternative drug delivery technique explored in this study has its potential applications in intracellular and topical fungal infections, and infections with highly resistant fungi. Infections by intracellular fungi like *Histoplasma capsulatum* and *Cryptococcus neoformans* are difficult to treat because of difficulty in transport through cell membranes and decreased activity inside the cells. PHMB based drug delivery system offers a less expensive solution compared to the existing ones and allows for lower doses of antifungal agents to be used.

It is envisaged that the PHMB (or indeed similar polymers capable of forming nanoparticles can be combined with antifungal agents to target the fungi listed in Table 4 below.

TABLE 4

| GENUS | SPECIES |
|---|---|
| *Trichophyton* | *mentagrophytes* |
| *Trichophyton* | *rubrum* |
| *Epidermophyton* | *floccosum* |

Nanoparticle Formation with Terbinafine and PHMB

Experiments were conducted to form nanoparticles formed with Terbinafine and PHMB.

Terbinafine was dissolved in DMSO to a stock concentration of 10 mg/ml. It was then further diluted to a 1 mg/ml concentration in ultrapure water (20 ul 10 mg/ml Terbinafine was added to 180 ul $H_2O$) and mixed thoroughly by vortexing).

PHMB (1 mg/ml in water) was heated for 20 mins at 60° C. and then allowed to cool to room temperature prior to use.

The ratio of PHMB:Terbinafine was kept constant at 3:1 as this provided the optimum nanoparticle size and numbers in the conditions tested to date.

PHMB/Terbinafine Nanoparticle Formulation:

A ten times nanoparticle formulation of 30:10 (ug/ml PHMB:Terbinafine) was made up in 300 ul. 288 µl of PBS was added to a 1.5 ml sterile tube. 9 µl 1 mg/ml PHMB was added and mixed by pipetting up and down 5 times. 3 ul of 1 mg/ml Terbinafine was then added slowly and mixed by pipetting up and down 5 times. The incubation was then left for 1 hour at room temperature in the presence of PHMB to form nanoparticles.

The solution was then further diluted ten fold with PBS for measurement on the Nanosight LM10 nano particle sizing machine (to give a final concentration of 3 ug/ml PHMB and 1 ug/ml Terbinafine).

Measurements were read on the Nanosight LM10 machine (obtained from Nanosight Limited, Wiltshire, UK) for 1 minute at 20° C., camera level 9, screen gain 10 and a detection threshold 6.

Figure 8:
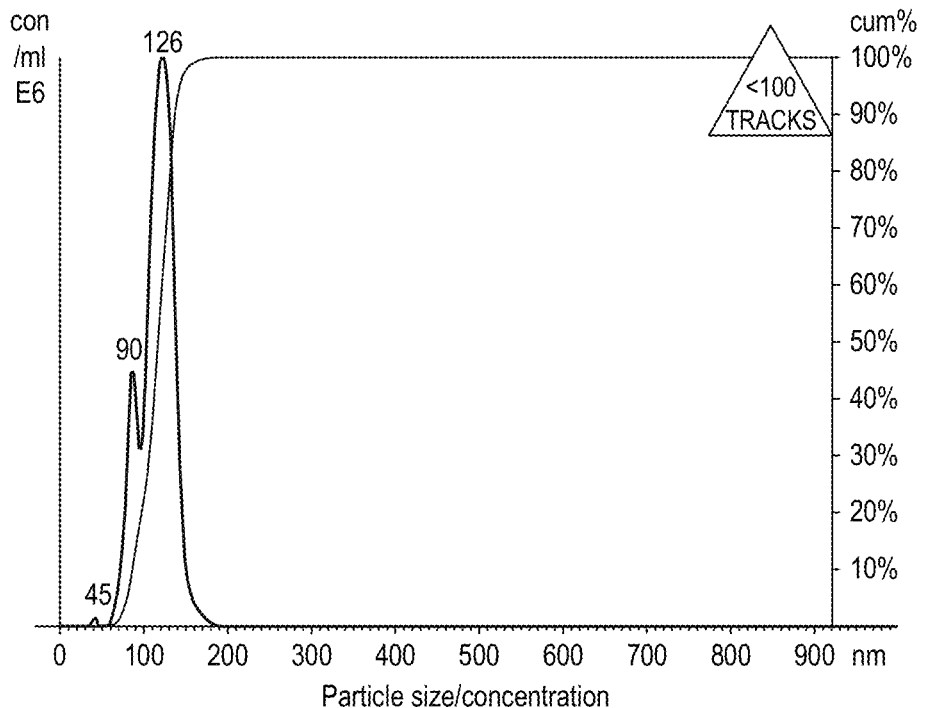
FIG. 8 is a graph showing the nanoparticle size/concentration of nanoparticles produced comprising Terbinafine and PHMB.
Figure 9:
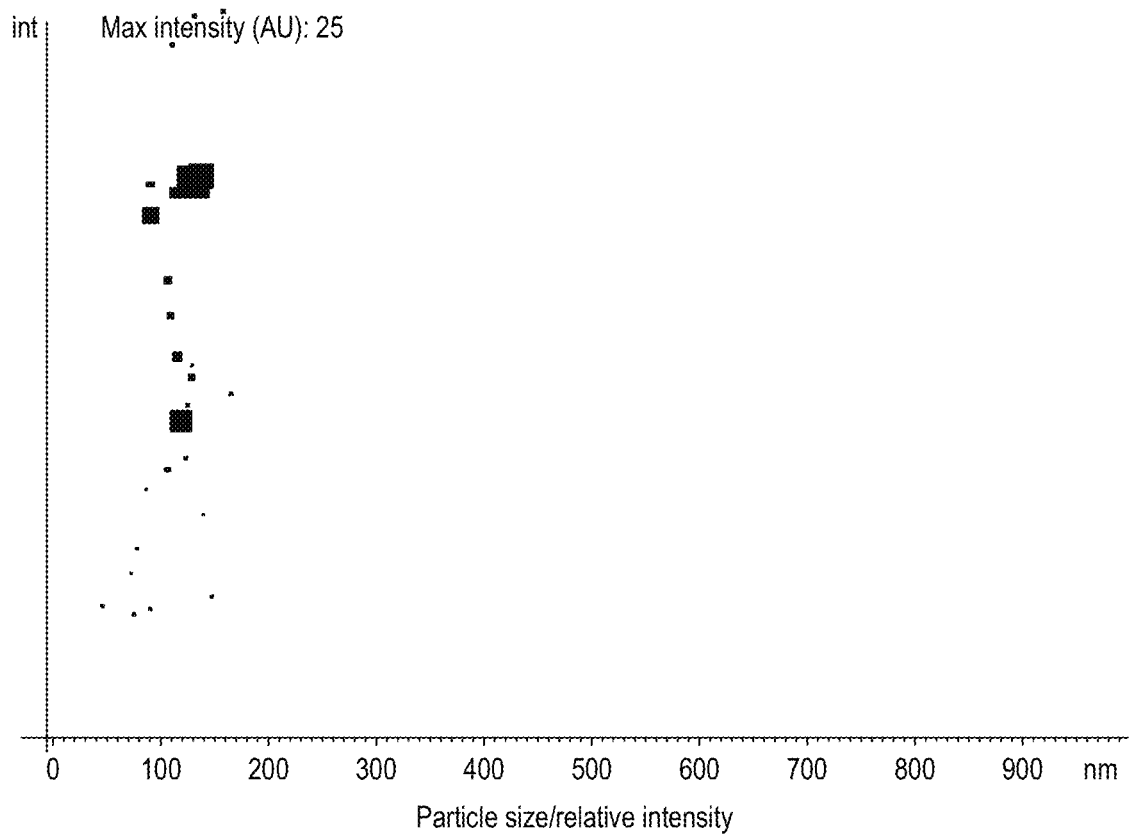
FIG. 9 is a graph showing the nanoparticle size/relative intensity of nanoparticles produced comprising Terbinafine and PHMB.

The results of the Nanosight are shown in FIGS. 8 to 10 and are summarized in below in Table 5:

TABLE 5

Size Distribution: Mean: 119 nm, Mode: 126 nm, SD: 18 nm
Cumulative Data (nm): D10: 90, D50: 121, D90: 141, D70: 130
User Lines: 0 nm, 0 nm
Total Concentration: 1.27 particles/frame, 0.14E8 particles/ml
Selected Concentration: 0.00 particles/frame, 0.00E8 particles/ml
Fitted Curve: Mean: 0 nm, SD: 0
Completed Tracks: 27
Drift Velocity: 1331 nm/s As shown in FIGS. 8-10, nanoparticles comprising PHMB and Terbinafine and PHMB were produced which could then be used in the preparation of a topical medicament for the subsequent treatment of a range of potential fungal infections.

Micro-Needle Patch

Transdermal patches have long been used for the administration of small-molecule lipophilic drugs that can be readily absorbed through the skin. This non-invasive delivery route is advantageous for the administration of many drugs incompatible with oral delivery, as it allows for direct absorption of the drug into the systemic circulation, by-passing both the digestive and hepatic portal systems which can also dramatically reduce the bioavailability of many drugs. Transdermal delivery also overcomes many of the challenges associated with subcutaneous injection by greatly reducing patient discomfort, needle anxiety, risk of accidental needle stick injury to the administrator and issues surrounding sharps disposal.

Despite these many advantages, transdermal delivery of drugs is confined to classes of molecules compatible with absorption through the skin. Delivery of small molecule salts and therapeutic proteins are not typically viable with traditional transdermal delivery, as the skin provides an effective protective barrier to these molecules even in the presence of absorption-enhancing excipients. However, micro-needle technology can be employed to deliver the nanoparticles containing antifungal agents directly to the epidermis, dermis and the nail matrix (where the nail and skin meet at the eponychium). By delivering the composition of the invention in this way, the nanoparticles will enter the nail matrix and capillary system and deliver the antifungal nanoparticle composition to the nail bed, under the hard nail plate, and into the fungi. In this way the potent antifungal agents can be directly delivered to the site of action thus reducing the treatment time and enhancing the potency.

FIGS. 11 and 12 show diagrams of a finger 10 to which a micro-needle patch (illustrated in FIG. 13) can be applied to a finger within the treatment area 12 shown by a dotted line. The treatment area 12 is formed of the dermis behind the nail 14 and also at the nail matrix (eponychium) 16 where the nail and skin meet. The nail root 18 is located in the area under the dermis behind the nail and can therefore be treated effectively by applying a micro-needle patch for delivering the composition of the present invention. Of course, the micro-needle patch could be used for toe nails in addition to finger nails.

FIG. 13 shows a diagram of a micro-needle patch which can be used to apply the composition of the present invention to an individual suffering from a fungal nail infection. The micro-needle patch 20 is formed of a flexible web of material 22 having an adhesive 24 applied to its underside. Centrally located on the underside of the flexible web is an array of downwardly extending micro-needles 26 having a plurality of points 30. The points can be formed as needles having conduits which are connected to a reservoir 28 containing the composition or simply have their points coated in the composition. In an alternative configuration, a reservoir 28 can expel the composition through holes disposed about the micro-needle arrays so that the composition can continuously coat the points of the array over a predetermined time frame. It will be apparent to the skilled addressee that a number of different micro-needle patches are currently available and that the composition of the present invention could be adapted for use with a range of them.

The micro-needles, can be less than 2 mm in length, and preferably about 250 μm will be inserted into the skin with minimum patient discomfort and, given the small hole created, with minimal risk of post-injection infection, bleeding, or risk of inadvertent IV injection for an intradermal administration. In addition, micro-needles reduce risk to the injection administrator, as accidental puncture of the skin is nearly impossible with these small projections.

It is envisaged that the micro-needle patch could be used for a single treatment where all the patient has to do is remove the patch from a wrapper and apply it to the appropriate part of the finger or toe for a given period of time. In the alternative, the micro-needle patch could be sold in combination with the composition and the patient would coat a quantity of the composition onto the surface of the micro-needles and apply the patch to the body in the prescribed manner. The patch could come with markings on its exterior so as to assist the patient or physician correctly line up the micro-needles with the correct location on the finger or toe to be treated.

Aerosol

The composition of the invention can also be formulated into an aerosol formulation.

In this worked example, PHMB nanoparticles are formed with caspofungin (a lipopeptide antifungal) and dried. The dried nanoparticles are then added to a propellant. The propellant provides the force to generate the aerosol cloud and is also the medium in which the caspofungin nanoparticle active component are be suspended or dissolved.

A range of propellants may be used, but generally speaking must have:
- a boiling point in the range −100 to +30° C.
- a density of approximately 1.2 to 1.5 g cm$^{-3}$ (approximately that of the drug to be suspended or dissolved)
- a vapour pressure of 40 to 80 psig
- no toxicity to the patient
- be non-flammable
- be able to dissolve common additives. Active ingredients should be either fully soluble or fully insoluble.

Propellants which are used in asthma inhalers will be particularly suitable, such hydrofluoroalkanes (HFA): either HFA 134a (1,1,1,2,-tetrafluoroethane) or HFA 227 (1,1,1,2,3,3,3-heptafluoropropane) or combinations thereof. Additionally, or alternatively, phospholipids that enhance penetration and bioavailability may be utilised.

The nanoparticles will reconstitute when the moisture is added, for example when the preparation is sprayed into the moist environment of the lungs. It is preferred that preparation is contained in an aluminium alloy vessel which is internally coated with fluoropolymer and sealed with a metering valve so that a metered dose can be dispensed. If required, an atomising nozzle and dustcap may also be fitted.

The forgoing embodiments are not intended to limit the scope of the protection afforded by the claims, but rather to describe examples of how the invention may be put into practice.

The invention claimed is:

1. A topical composition for the treatment of a fungal nail or skin infection comprising nanoparticles comprising a polymer and an antifungal agent, wherein the polymer comprises polyhexamethylene biguanide and the antifungal agent comprises terbinafine, wherein a ratio of the polyhexamethylene biguanide to terbinafine is about 3:1.

2. A topical composition as claimed in claim 1, wherein the antifungal agent is present in a dosage amount within the composition, which is less than the therapeutically effective systemic dose of the antifungal agent.

3. A topical composition as claimed in claim 1, wherein the composition further comprises one or more of the following component: buffers, excipients, binders, oils, water, emulsifiers, glycerin, antioxidants, preservatives and fragrances.

4. A topical composition as claimed in claim 3, wherein the composition further comprises urea.

5. A topical composition as claimed in claim 1, wherein the fungal skin infection comprises athlete's foot.

6. A topical composition as claimed in claim 1, wherein the antifungal agent comprises one or more further agents selected from the following group: Nystatin, Ketoconazole, Amphotericin B, Itraconazole or Berberine.

7. A topical composition as claimed in claim 1, wherein the fungal infection comprises a dermatophytic and/or yeast infection.

8. A topical composition as claimed in claim 1, wherein the composition is in the form of a cream, ointment, spray or powder.

9. The topical composition as claimed in claim 1, wherein the composition is present in a solution in which the concentration of PHMB is 3 µg/ml and the concentration of terbinafine is 1 g/ml.

\* \* \* \* \*